US010520404B2

(12) United States Patent
Sim et al.

(10) Patent No.: US 10,520,404 B2
(45) Date of Patent: Dec. 31, 2019

(54) BIOMOLECULE EXTRACTION DEVICE AND BIOMOLECULE EXTRACTION METHOD

(71) Applicant: L'OREAL, Paris (FR)

(72) Inventors: Woo-Young Sim, Gyeonggi-do (KR); Yu-Rae Kim, Gyeonggi-do (KR); Jae-Jeong Kim, Gyeonggi-do (KR); Eun-Ji Lee, Gyeonggi-do (KR)

(73) Assignee: L'OREAL, Paris (FR)

( * ) Notice: Subject to any disclaimer, the term of this patent is extended or adjusted under 35 U.S.C. 154(b) by 442 days.

(21) Appl. No.: 14/905,268

(22) PCT Filed: Jul. 17, 2014

(86) PCT No.: PCT/KR2014/006515
§ 371 (c)(1),
(2) Date: Jan. 14, 2016

(87) PCT Pub. No.: WO2015/009085
PCT Pub. Date: Jan. 22, 2015

(65) Prior Publication Data
US 2016/0153876 A1  Jun. 2, 2016

(30) Foreign Application Priority Data
Jul. 17, 2013 (KR) .................. 10-2013-0084110

(51) Int. Cl.
*G01N 1/31* (2006.01)
*B01L 3/00* (2006.01)
(Continued)

(52) U.S. Cl.
CPC .......... *G01N 1/31* (2013.01); *A61B 5/150343* (2013.01); *B01L 3/502* (2013.01);
(Continued)

(58) Field of Classification Search
None
See application file for complete search history.

(56) References Cited

U.S. PATENT DOCUMENTS 6,649,378 B1 * 11/2003 Kozwich ................ B01L 3/502
422/68.1
8,221,381 B2 * 7/2012 Muir ...................... B01L 3/502
604/415
(Continued)

FOREIGN PATENT DOCUMENTS

CN          1967195 A      5/2007
CN       201459139 U      5/2010
(Continued)

OTHER PUBLICATIONS

Thiele et al, Protein oxidation in human stratum corneum: susceptibility of keratins to oxidation in vitro and presence of a keratin oxidation gradient in vivo; journal of investigative dermatology; vol. 113, issue 3; pp. 335-339; published 1999.*
(Continued)

*Primary Examiner* — Benjamin R Whatley
(74) *Attorney, Agent, or Firm* — Arent Fox LLP

(57) ABSTRACT

A biomolecule extraction device and method for use thereof are disclosed. The biomolecule extraction device has an insertion part, a body part and at least on discharge port. The insertion port is insertable in a body part, and is configured to fix a sample of collected biomass containing biomolecules. The body part is configured to receive a lyses buffer and contact the surface of the fixed biomass with the lyses buffer to extract the biomolecules from the biomass when the insertion part is inserted in the body part. The at least one discharge part is disposed in the insertion part or the body part for discharging biomass lysate containing the extracted biomolecules.

14 Claims, 14 Drawing Sheets

(51) Int. Cl.
*G01N 1/34* (2006.01)
*G01N 35/00* (2006.01)
*C12N 15/10* (2006.01)
*A61B 5/15* (2006.01)
*C12M 1/00* (2006.01)

(52) U.S. Cl.
CPC ......... *C12M 47/10* (2013.01); *C12N 15/1003* (2013.01); *G01N 1/34* (2013.01); *G01N 35/00009* (2013.01); *B01L 2200/0689* (2013.01); *B01L 2200/087* (2013.01); *B01L 2200/141* (2013.01); *B01L 2300/044* (2013.01); *B01L 2300/0609* (2013.01); *B01L 2300/08* (2013.01); *B01L 2400/0481* (2013.01)

(56) References Cited

U.S. PATENT DOCUMENTS

| | | | |
|---|---|---|---|
| 2002/0012982 A1 | 1/2002 | Blakesley et al. | |
| 2008/0193926 A1 | 8/2008 | Abraham-Fuchs et al. | |
| 2009/0258382 A1 | 10/2009 | Schultz et al. | |
| 2010/0285578 A1* | 11/2010 | Selden .............. | B01L 3/502715 435/325 |
| 2010/0298671 A1 | 11/2010 | Asakura et al. | |
| 2011/0212453 A1 | 9/2011 | Agarwal et al. | |
| 2011/0300609 A1 | 12/2011 | Lim et al. | |

FOREIGN PATENT DOCUMENTS

| | | |
|---|---|---|
| CN | 101900722 A | 12/2010 |
| CN | 102939453 A | 2/2013 |
| EP | 1574564 A1 | 9/2005 |
| JP | 9145710 A | 6/1997 |
| JP | 2002-532059 A | 10/2002 |
| JP | 2004-051170 A | 2/2004 |
| JP | 2004-504330 A | 2/2004 |
| JP | 3914970 B2 | 2/2007 |
| JP | 2009150830 A | 7/2009 |
| JP | 2010-271259 A | 12/2010 |
| JP | 2011-505011 A | 2/2011 |
| JP | 2013-519884 A | 5/2013 |
| KR | 10-2009-0021503 A | 3/2009 |
| KR | 10-1030848 B1 | 4/2011 |
| KR | 10-1049201 B1 | 7/2011 |
| WO | 200012675 A1 | 3/2000 |
| WO | 2009073152 A1 | 6/2009 |
| WO | 2010-024042 A1 | 3/2010 |

OTHER PUBLICATIONS

First China Office Action dated Mar. 21, 2017, regarding China Application No. CN201480040355.1, and English translation.
English translation of Table regarding First China Office Action dated Mar. 21, 2017, regarding China Application No. CN201480040355.1.
First Search Report regarding Mar. 21, 2017 First China Office Action, regarding China Application No. CN201480040355.1, and English translation.
EP Communication dated Feb. 24, 2016 regarding EP14826368.4.
EP Communication dated Mar. 14, 2017 regarding EP14826368.4.
EP Communication (Office Action) dated Sep. 20, 2017 regarding EP14826368.4.
EP Search Opinion dated Feb. 23, 2017 re EP14826368.4.
Supplementary EP Search Report dated Feb. 2, 2017, and attached Annex, re EP14826368.4.
Russian Office Action dated Oct. 27, 2017, re Russian Application No. 2016103926/10(006207).
Notification of Reasons for Refusal dated Apr. 11, 2018, regarding Japanese Patent Application No. JP 2016-527936.
Second Office Action dated Jan. 31, 2018, regarding Chinese Application No. CN201480040355.1.
EP Communication dated Apr. 26, 2018, regarding EP Application No. 14826368.4.
First Office Action dated May 15, 2018, regarding Australian Application No. AU2014290933.
Notification of Reasons for Refusal dated Dec. 4, 2018 regarding Japanese Appliction No. JP2016527936.

* cited by examiner

[Fig. 1]
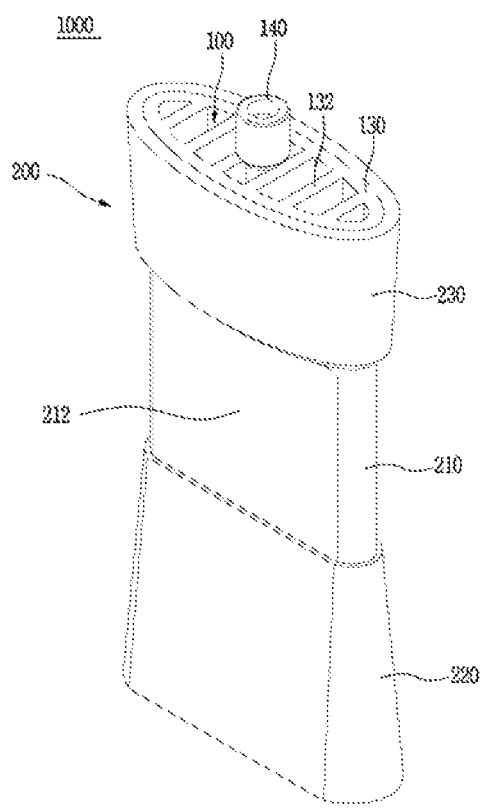

[Fig. 2]
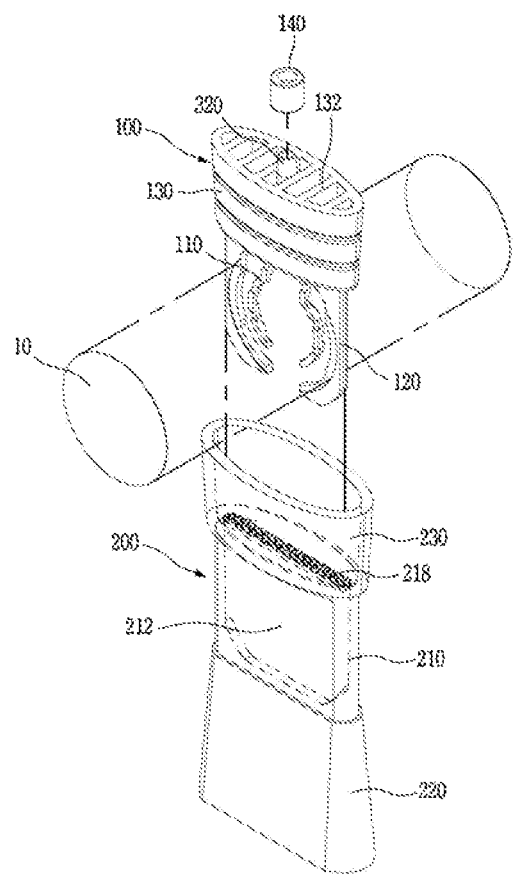

[Fig. 3]
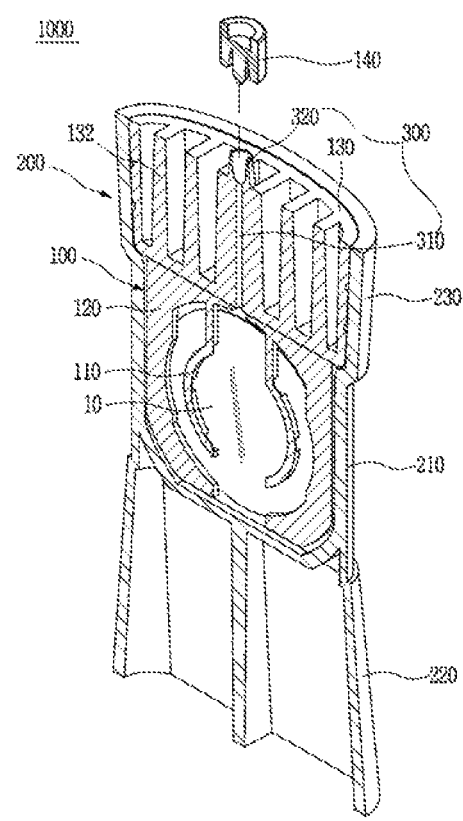

[Fig. 4]
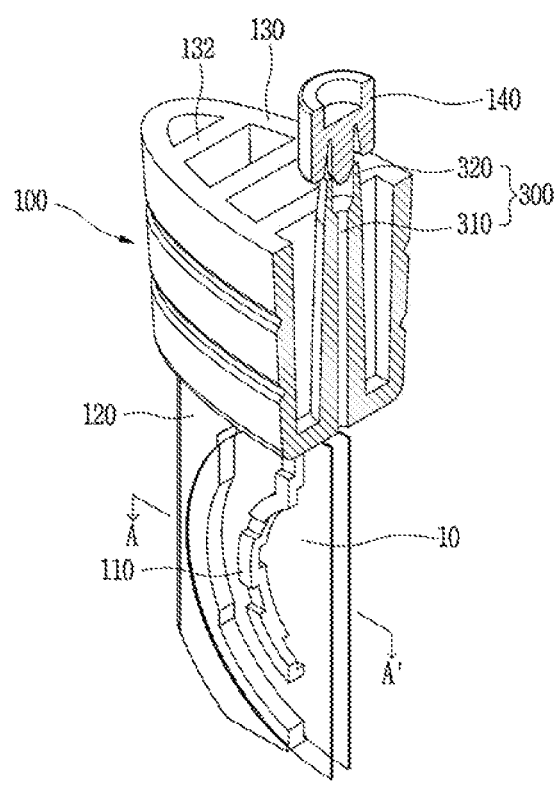

[Fig. 5]
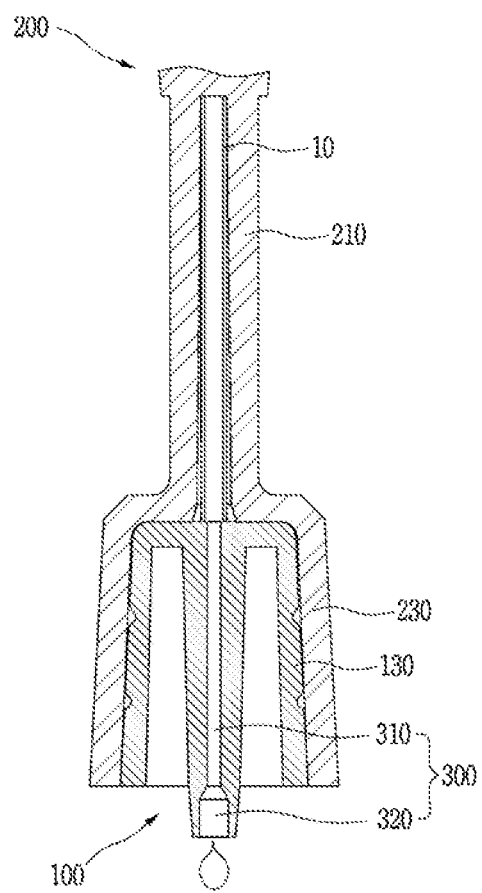

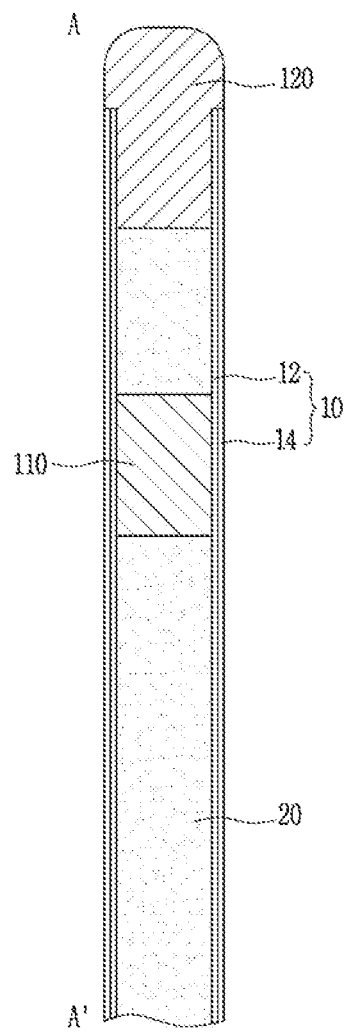
[Fig. 6]

[Fig. 7]
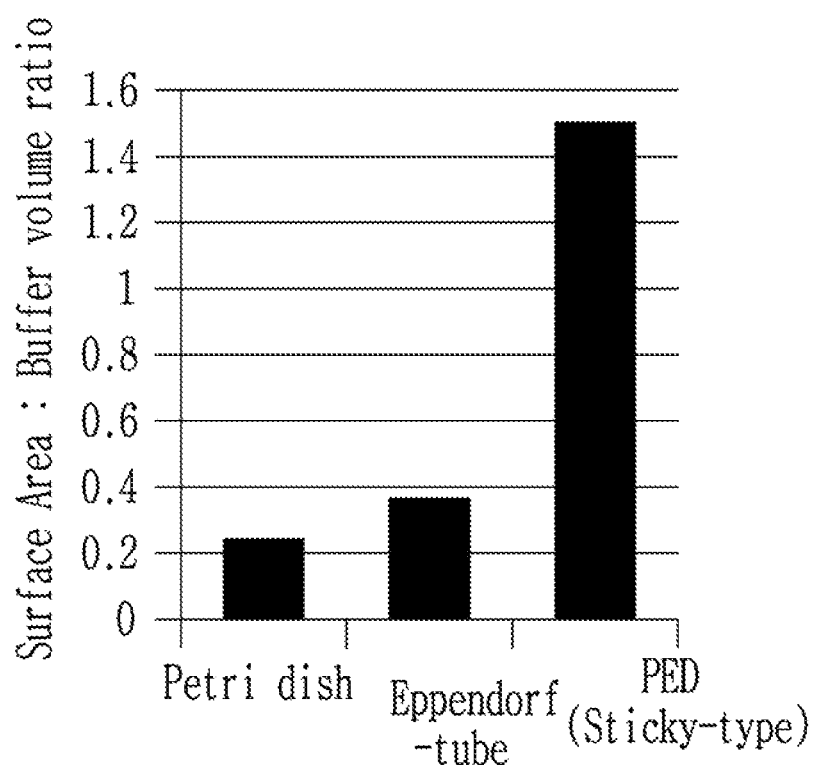

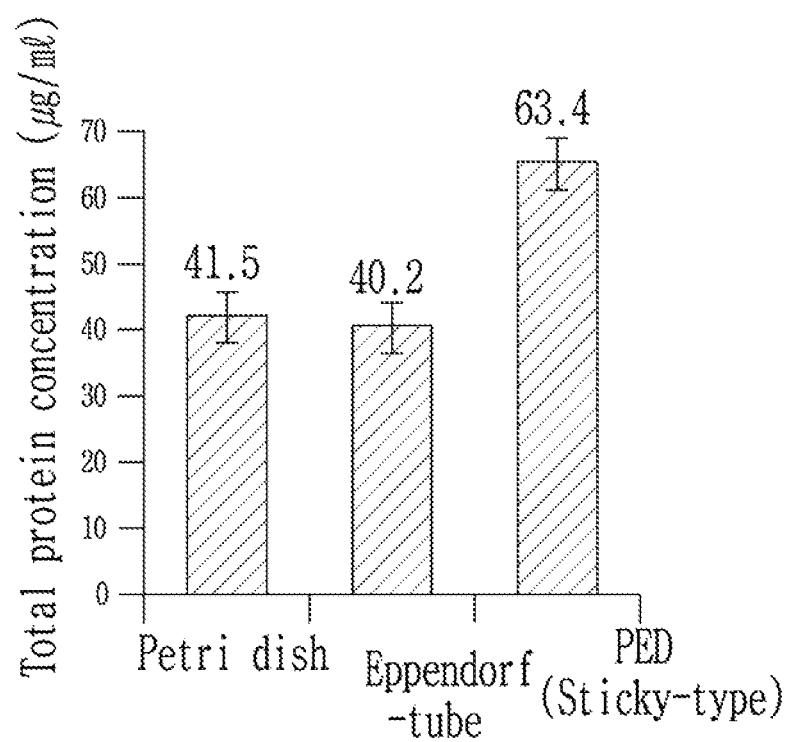
[Fig. 8]

[Fig. 9]
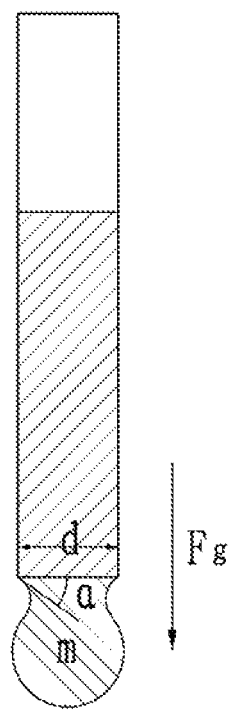

[Fig. 10]
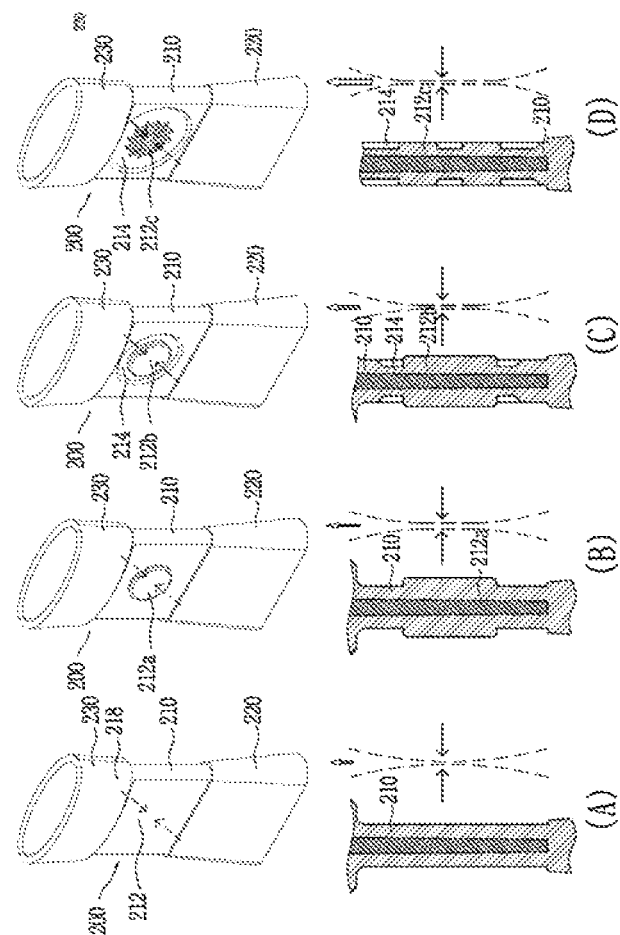

[Fig. 11]
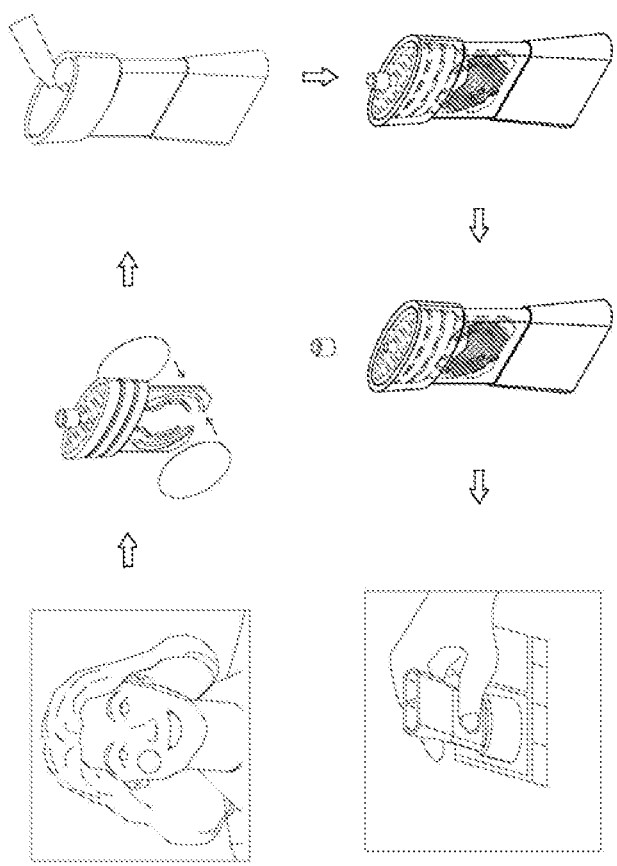

[Fig. 12]
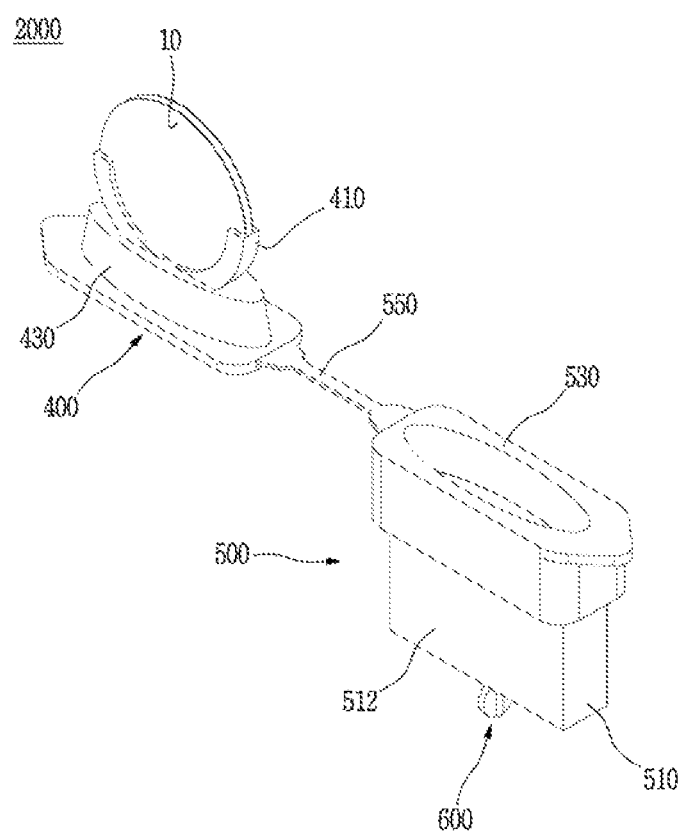

[Fig. 13]
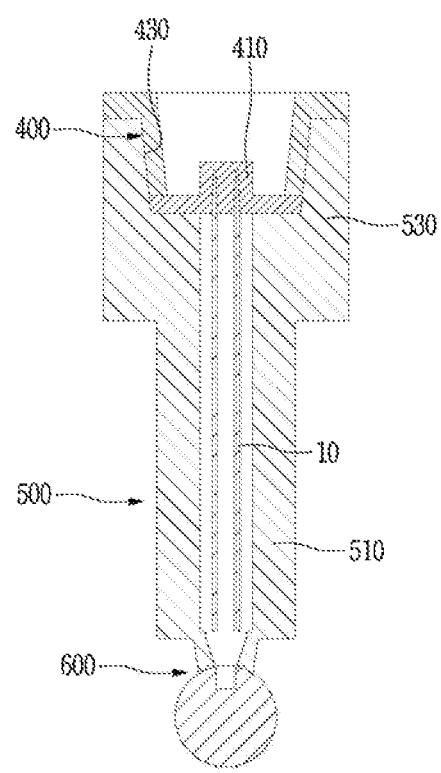

[Fig. 14]
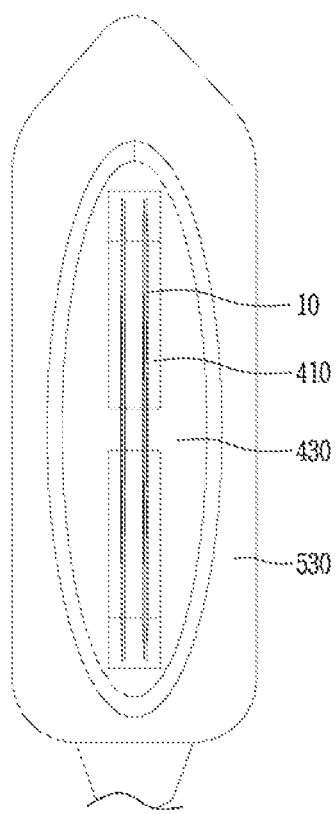

BIOMOLECULE EXTRACTION DEVICE AND BIOMOLECULE EXTRACTION METHOD

CROSS-REFERENCE TO RELATED APPLICATIONS

This application is a 371 National Stage Entry of PCT application PCT/KR2014/006515 filed Jul. 17, 2014, entitled "BIOMOLECULE EXTRACTION DEVICE AND BIOMOLECULE EXTRACTION METHOD," which is based from and claims priority to KR 10-2013-0084110 filed Jul. 17, 2013, both of which are hereby expressly incorporated by reference in their entireties.

BACKGROUND OF THE INVENTION

Field of the Invention

The present invention relates to a biomolecule extraction device and biomolecule extraction method. More specifically, it relates to a biomolecule extraction device and biomolecule extraction method that can enhance a user's convenience by simplifying the process of extracting a biomolecule, such as a protein or a nucleic acid, etc., from a biomass sample, such as tissue and cell samples, with a lyses buffer, and saving time spent. As the ratio of the surface area of the sample to the amount of lysis buffer introduced is maximized, the concentration of biomolecule extraction is increased and the amount of buffer used is minimized. The present invention can also smoothly perform efficient testing without extra device or equipment by allowing constant discharge of the biomass lysate containing the extracted biomass.

Description of Related Art

Cell lysis refers to a phenomenon where a cell membrane is ruptured and cell contents (cytoplasma) are exposed as the cell dissolves. Such cell lysis is a primary process for cell analysis and protein purification, and is widely used not only to extract/separate protein, but also to separate nucleic acid, such as DNA (deoxyribonucleic acid) or RNA (ribonucleic acid) prior to an amplification process, such as the PCR (polymerase chain reaction), used in molecular biology and molecular diagnostics, etc.

Cell lysis methods for cell disruption largely include optical, acoustic, electrical and mechanical methods. Mostly, the methods are carried out in a form applying external force and stress in various mechanical and physical manners based on a lysis buffer.

Optical cell lysis is a method for destroying cells by irradiating laser micropulse on the target cells to form cavitation bubbles and destroying cells as the cavitation bubbles expand. Optical cell lysis has disadvantages in that there is a possibility for the cell and protein to be degenerated due to the heat abruptly generated by applying a laser inside a specific cell or at a nearby location, and that a separate device for generating laser micropulses must be used should be added.

Acoustic cell lysis is a method for destroying cells by introducing a cell solution or a suspension inside a chamber located in an ultrasonic water tank and applying ultrasonic waves. It is difficult to obtain consistent results for cell destruction using ultrasonic waves because it is difficult to form uniform energy distribution of ultrasound waves, it takes a lot of time for cell destruction, and the cell destruction using ultrasound waves may cause protein destruction or deformation due to the heat generated.

Electrical cell lysis is a method destroying cells by applying an electric field to the cells to generate potential difference in cell membrane. It is similar in a way to other cell lysis methods such as the freezing-thawing method, heating method, osmotic pressure impact method, in terms of applying impact to cell walls. However, these methods have problems that protein in the cells may be damaged due to the thermal impact applied to the cells.

Mechanical cell lysis uses presses, bead mills, etc. To be specific, presses perform cell disruption by filling an empty cylindrical body made of stainless steel often used in laboratory scale with cell paste, and extracting the cells to atmospheric pressure through a needle valve on the bottom of the cylinder under high pressure.

High-speed bead mills comprise a grinding chamber filled with small glass or iron beads (20~50 units), and grind cells with high shearing force and impact force by rotating a circular disk or impeller attached to a driving shaft by a motor and stirring the beads.

Such mechanical cell lysis has problems that it is difficult to apply the mechanical cell lysis to a small amount of samples, and expensive equipment, large space, multi-step process and long processing time are required.

Meanwhile, a homogenizer performs cell lysis and disruption by having a user rotate a stick while filling an E-tube (Eppendorf-tube) or falcon tubes of various capacities, etc. with a lysis buffer. In this regard, there may be problems that in order to immerse a tape or disk for obtaining samples, a relatively large amount of lysis buffer is required and the sample may splash out or the buffer may overflow while rotating the stick.

In addition, there are problems that in case of using the E-tube (Eppendorf-tube) or Petri dish itself, in order to apply the lysis buffer to a hydrophobic sample, a relatively large amount of buffer is required and additional work such as several times of pipetting, etc. using tools such as a pipette is required.

Meanwhile, cell lysates according to cell lysis are widely used for special protein detection tests (western blotting) or immune precipitation, etc., and in case of extracting nucleic acid (DNA, RNA), they are applied to molecular diagnostics and gene analysis, etc. using PCR or sequencing. The above processes are performed by detecting the special protein itself or testing interaction between molecules.

Here, for cell lysis, it is preferable to have a sufficient amount of biomolecule (protein or nucleic acid, etc.) product extracted from biomass, high purification concentration, and no loss or deformation of the extract. For doing so, an expensive protease inhibitor, etc. is used. Thus, since cell lysis of good quality for biomass sample should be performed fast and analyzed immediately, it would be necessary to simplify the process of extracting biomolecule and save cost and time spent therefor.

However, as mentioned above, the conventional biomolecule extraction devices and methods thereof through cell lysis and disruption required an extra device or equipment such as a centrifugal separator and pipette, etc. while performing each steps. Plus, a complex process associated with the system had to be performed, thereby requiring a lot of space, cost and time.

Also, in case of using a tape or disk for obtaining samples, there are problems that a lysis buffer where the sample can be immersed is required in order to maximize the contact surface of the sample and that due to the decrease in extraction concentration by applying a large amount of lysis buffer, a large amount of samples, i.e., biomass needs to be collected and additional work of chopping or dissociating the sample is required.

This still leaves the problem of processing the residue which may contaminate the environment and affect human safety, after extracting biomolecule such as protein or nucleic acid from the sample.

Thus, the necessity of a biomolecule extraction device has been raised where user's convenience can be enhanced by saving time and reducing space in need, resulted from simplifying the process of extracting biomolecule from biomass, and where consistent test results can be expected by minimizing the damage of the extracted biomolecule and extracting at a relatively high concentration while applying only a small amount of samples.

Further, the biomolecule extraction device can not only increase the concentration of biomolecule extracted and reduce the amount of buffer used by minimizing dead space thereby maximizing the ratio of the surface area of the sample to the amount of lysis buffer introduced, but can also efficiently and smoothly perform testing by allowing constant biomass lysate containing the extracted biomass.

SUMMARY OF THE INVENTION

Subject Matter to be Solved

The examples of the present invention are intended to simplify the process of extracting biomolecule, such as protein or nucleic acid, etc., from biomass such as tissue and cell and save time and space spent therefor to enhance user's convenience.

Also, the examples of the present invention are intended not only to increase the concentration of biomolecule extracted and reduce the amount of buffer used by minimizing dead space thereby maximizing the ratio of the surface area of the sample to the amount of lysis buffer introduced.

In addition, the examples of the present invention are intended to provide a biomolecule extraction device and method thereof that can be independently used without requiring an extra device or equipment to be applied, minimize damage of the extracted biomolecule, and expect consistent test results while applying only a small amount of samples.

Means for Solving Subject Matter

According to an aspect of one example in various applications of the present invention, a biomolecule extraction device may be provided, comprising an insertion part to which a sample containing collected biomass is fixed, a body part which receives a lysis buffer inside and into which the insertion part is inserted to extract biomolecule from the collected biomass, and at least one discharge part provided at the insertion part or the body part.

The insertion part comprises at least one fixing part to which the sample is fixed.

Also, the fixing part fixes the sample by adhesive bonding or physical bonding.

Adhesive bonding of the fixing part is performed by using the adhesiveness present in the collected sample or applying an adhesive substance to the fixing part.

Here, at least part of the fixing part is in a bent curved shape.

Physical bonding of the fixing part fixes the sample by insertion bonding.

At least part of the sample is fixed to the fixing part.

The body part comprises a chamber having a predetermined space formed inside for receiving the lysis buffer and into which the insertion part is inserted and the lysis buffer is immersed.

Here, the composition and component of the lysis buffer may vary depending on the type of the biomolecule to be extracted.

The biomolecule extraction device according to an aspect of the present invention further comprises a shielding film sealing the entrance of the chamber wherein the lysis buffer is received in the chamber in a sealed condition. In some cases, a lysis buffer of a certain amount required for a separate disposable container may be provided in a sealed condition.

Meanwhile, the body part further comprises an introduction part guiding the insertion part to the chamber.

Here, the insertion part comprises a sealing part formed in a form corresponding to the introduction part and having a close contact with the inner wall of the introduction part to seal the chamber.

Also, the cross sections of the introduction part and the sealing part are formed in an oval or circular shape.

Also, the sealing part comprises a reinforcing rib for reinforcing strength thereof.

The discharge part comprises a discharge flow path and an expanded discharge port for constantly discharging the biomass lysate containing the extracted biomass.

The discharge flow path has an inner diameter smaller than the discharge port in order to minimize dead space.

The biomolecule extraction device according to an aspect of the present invention may further comprise a sealing cap detachably sealing the discharge part.

The biomolecule extraction device according to an aspect of the present invention may further comprise a pressing part being formed at the outer wall of the chamber and applying pressure allowing constant discharge of the biomass lysate containing the extracted biomolecules.

Here, the pressing part is formed in an embossed form having a thickness greater than that of the surrounding outer wall.

Also, the biomolecule extraction device according to an aspect of the present invention may further comprise an engraved part being formed around the pressing part and having a thickness smaller than the surrounding outer wall.

Here, a ratio between the surface area of the sample in contact with the lysis buffer and the volume of the lysis buffer is from 0.4 to 9.15.

According to another aspect of the present invention, the present invention may provide a method for extracting biomolecule, comprising fixing a sample containing collected biomass to an insertion part, inserting the insertion part into the body part receiving lysis buffer inside, and biomass lysate containing biomolecule extracted from the biomass through a discharge part provided at any one of the insertion part or the body part.

According to another aspect of the present invention, the extraction device comprises a chamber receiving a lysis buffer inside and an insertion part being inserted inside the chamber together with the two tapes for obtaining samples containing collected biomass which are adhered to the insertion part while being separated from each other and facing each other, wherein the non-adhesive surfaces of the two tapes for obtaining samples are respectively adhered to both inner walls of the chamber and the lysis buffer can fill in the space between the adhesive surfaces of the two tapes for obtaining samples.

According to another aspect of the present invention, a tape for obtaining samples containing collected biomass is inserted in the lysis buffer received inside the chamber and the collected biomass is dissolved. A ratio between the surface area of the tape for obtaining sample in contact with the lysis buffer and the volume of the lysis buffer received inside the chamber may be from 0.4 to 9.15.

Effect of the Invention

The examples of the present invention are intended to simplify the process of extracting biomolecule such as protein or nucleic acid, etc. from biomass such as tissue and cell and save time and space spent therefor to enhance user's convenience.

Also, the examples of the present invention are intended not only to increase the concentration of biomolecule extracted and reduce the amount of buffer used by minimizing dead space thereby maximizing the ratio of the surface area of the sample to the amount of lysis buffer introduced.

In addition, the examples of the present invention are intended to provide a biomolecule extraction device and method thereof that can be independently used without requiring an extra device or equipment to be applied, minimize damage of the extracted biomolecule, and expect consistent test results while applying only a small amount of samples.

BRIEF DESCRIPTION OF THE DRAWINGS

FIG. 1 is a perspective view of the biomolecule extraction device according to an embodiment a first aspect of the present invention.

FIG. 2 is an exploded perspective view of the biomolecule extraction device according to the first aspect of the present invention.

FIG. 3 is a cut perspective view cutting the biomolecule extraction device according to the first aspect of the present invention in the major axis direction thereof.

FIG. 4 is a cut perspective view cutting the insertion part of the biomolecule extraction device according to the first aspect of the present invention in the minor axis direction thereof.

FIG. 5 is a cross sectional view illustrating the state of constant discharge of the biomass lysate containing the extracted biomolecule after inserting the insertion part of the biomolecule extraction device according to the first aspect of the present invention into the body part.

FIG. 6 is a cross sectional view of A-A' of FIG. 4.

FIG. 7 is a graph comparing the Surface Area:Volume ratio of the biomolecule extraction device according to the first aspect of the present invention with the conventional methods.

FIG. 8 is a graph comparing the extraction concentration of the biomolecule extraction device according to the first aspect of the present invention with conventional methods.

FIG. 9 is a diagram illustrating variables for designing an expanded discharge port for constant discharge after extracting the sample.

FIG. 10 illustrates perspective views and partial cross sectional views of modifications examples of the pressing part of the biomolecule extraction device according to the first aspect of the present invention, and diagrams illustrating deformation of the inner walls of the chamber when pressed.

FIG. 11 is process diagram illustrating the process of extracting protein using the biomolecule extraction device suggested according to a second aspect of the present invention.

FIG. 12 is a perspective view of the biomolecule extraction device according to ea third aspect of the present invention.

FIG. 13 is a cross sectional view of the biomolecule extraction device according to a fourth aspect of the present invention.

FIG. 14 is a plan view of the biomolecule extraction device according to embodiment fifth aspect of the present invention.

DETAILED DESCRIPTION

Hereinafter, with reference to the attached drawings, various embodiments of the present invention will be described in detail. However, the present invention is not limited to the aspects described here, but may be realized in other forms. In fact, the aspects introduced here are provided to complete the disclosure thoroughly and sufficiently deliver the idea of the present invention to a person having ordinary skill in the art. Throughout the specification, the same reference numerals refer to the same constitutional elements.

FIG. 1 is a perspective view of the biomolecule extraction device according to an aspect of the present invention. FIG. 2 is an exploded perspective view of the biomolecule extraction device according to the aspect of the present invention. FIG. 3 is a cut perspective view cutting the biomolecule extraction device according to the aspect of the present invention in the major axis direction thereof. FIG. 4 is a cut perspective view cutting the insertion part of the biomolecule extraction device according to the aspect of the present invention in the minor axis direction. FIG. 5 is a cross sectional view illustrating the state of constant discharge of the biomass lysate after inserting the insertion part of the biomolecule extraction device according to the aspect of the present invention into the body part. FIG. 6 is a cross sectional view of A-A' of FIG. 4. FIG. 7 is a graph comparing the surface area:volume ratio of the biomolecule extraction device according to the embodiment of the present invention with the conventional methods. FIG. 8 is a graph comparing the extraction concentration of the biomolecule extraction device according to the aspect of the present invention with the conventional methods. FIG. 9 is a diagram illustrating variables for designing an expanded discharge port for constant discharge after processing the sample.

Referring to FIGS. 1~9, the biomolecule extraction device (1000) according to an another aspect of the present invention may largely comprise an insertion part (100) to which a sample containing collected biomass is fixed, a body part (200) which receives a lysis buffer inside and into which the insertion part (100) is inserted to extract biomolecule from the collected biomass, and at least one discharge part (300) provided at the insertion part (100) or the body part (200).

The insertion part (100) may comprise at least one fixing part (110, 120) to which the sample is fixed. The fixing part (110, 120) may fix the sample by adhesive bonding or physical bonding, and the sample collecting biomass may be properly applied, for example, to a tape or membrane, etc. having an adhesive surface depending on the collection method.

In case the fixing part (110, 120) fixes the sample by adhesive bonding, a tape with an adhesive surface, for example, a tape for obtaining samples (10) having an adhesive surface coated with an adhesive substance, etc., is used, and bonded to the fixing part using the adhesiveness left on the tape after collecting sample. Alternatively, it may be configured to apply the adhesive substance to the fixing part (110, 120) and fix a non-adhesive sample.

In case the fixing part (110, 120) fixes the sample by physical bonding, it can be fixed by insertion. This will be explained in another aspect.

In one aspect, a tape for obtaining samples (10) is used, and the insertion part (100) may comprise the fixing part (110, 120) adhered by having at least part of the tape for obtaining samples (10) in contact.

Here, the fixing part (110, 120) may comprise a first fixing part (110) formed on the inner side and a second fixing part (120) formed on the outer side of the first fixing part (100). The fixing part may comprise two of each of the first fixing part (110) and the second fixing part (120) on the same plane in a form extended perpendicularly downwards.

Also, the two tapes for obtaining samples (10) may be adhered to face each other with the first fixing part (110) and second fixing part (120) interposed. The tape for obtaining samples (10) may be in a disk form. In fact, it is possible to use products such as D-Squame disk manufactured by Cuderm of USA.

One side of the tape for obtaining samples (10) can be an adhesive surface (12) and the other side can be a non-adhesive surface (14). If the adhesive surface (12) of the tape for obtaining samples (10) is attached to and then detached from the subject's skin, skin tissue comprising dead skin cells is collected by being attached to the adhesive surface (12), and protein can be extracted using this.

The two tapes for obtaining samples (10) containing collected skin tissue as above may be attached and fixed so that the adhesive surfaces (12) face each other as separated at a certain interval with the first fixing part (110) and second fixing part (120) interposed. Here, since the tapes for obtaining samples (10) are attached to be separated at a certain interval with the first fixing part (110) and second fixing part (120) interposed, and this prevents the tapes for obtaining samples (10) from being adhered to each other.

The two tapes for obtaining samples (10) are separated from each other as much as the thickness of the first fixing part (110) and second fixing part (120). When the insertion part (10) is inserted into the body part (200), a lysis buffer (20) fills in the space between the tapes for obtaining samples (10).

Thus, the thickness of the fixing parts (110, 120) becomes a separation distance between the two tapes for obtaining samples (10) and also a parameter for determining the volume of the lysis buffer (20) to be introduced.

Here, the first fixing part (110) and the second fixing part (120) may have the same thickness or the first fixing part (110) positioned on the inner side may have a thickness thinner than that of the second fixing part (120). In case a distance spaced enough not to be adhered to each other due to the rigidity of the tapes (10) is maintained, the first fixing part (110) may have a minimum thickness or even may be removed. In this case, the two tapes for obtaining samples (10) are spaced apart from each other by the thickness of the second fixing part (120) positioned on the other side. The part of the second fixing part (120) where the tape (10) is fixed has a size slightly greater than the outer circumference of the tape (10), and is engraved by the thickness of the tape, so that the insertion part (100) is not caught by protrusions of the tapes (10) or dead region is not generated when the insertion part (100) is inserted into the chamber (210) after the tapes (10) are fixed. Further, the first fixing part (110) positioned on the inner side prevents the tapes for obtaining samples (10) from being adhered to each other in their middle parts.

The first fixing part (110) and the second fixing part (120) may be made into a linear bar shape having a predetermined thickness, but in one aspect, at least part of it is in a bent curved shape. By configuring part of the first fixing part (110) and the second fixing part (120) to be in a curved shape, a user can apply pressure without interference by the first fixing part (110) or the second fixing part (120) when applying pressure to a pressing part (212, see FIG. 10) to be explained below. The structures of bumps are added to the first fixing part (110) as necessary, which enable to minimize the contact surface of the tapes for obtaining samples (10) and maximize the surface area of the tapes for obtaining samples (10) exposed to the lysis buffer (20), and allow free movement of the lysis buffer (20).

The body part (200) may comprise a chamber (210) which forms a predetermined space inside to receive the lysis buffer (20) and into which the tapes for obtaining samples (10) are inserted to be immerged in the lysis buffer (20).

A base (220) is provided in the lower part of the chamber (210) to support and stand the chamber (210). The base (220) may be formed with the slope such that the cross sectional area increases downward in order for the body part (200) to stand stably.

The thickness of the inside space of the chamber (210) is preferably configured such that each of non-contact surfaces (14) of the two tapes for obtaining samples (10) is adhered to the inner wall of the chamber (210) when the two tapes for obtaining samples (10) are inserted. Accordingly, most of the lysis buffer (20) contained in the chamber (210) fills the space between the two tapes for obtaining samples (10).

Such configuration is able to minimize dead space and to maximize the contact surface with the tapes for obtaining samples (10), which results in increasing the extraction concentration of biomolecule to a level which can be measured with a small amount of sample, even with applying a minimum amount of the lysis buffer (20).

In particular, conventionally, since skin tissue samples adhered to the tapes for obtaining samples (10) are hydrophobic and thus the lysis buffer (20) did not spontaneously spread out, external force should be compulsorily applied or additional operation should be performed by a device. Also, in order to avoid a problem that the tapes (10) rise up when immerged, external force should be consistently applied to the tapes (10).

Also, as explained above, the biomolecule extraction device (1000) according to one aspect of the present invention, which makes the contact surface with the tapes for obtaining samples (10) relatively very large with respective to the volume of the lysis buffer (20), can dissolve cells only by being shaken once or twice and being left to stand. When the insertion part (100) is inserted into and joined with the body part (200), strong fixing force can be maintained, and thus the lysis buffer (20) can fill the empty space between the tapes without additional compulsory external force or additional operation. The condition for contact can be effectively maintained. Thereby, the efficiency of extracting proteins can be rapidly increased.

These matters can be confirmed from the graphs of FIGS. 7 and 8. FIG. 7 compares the ratio (SA:V) of the surface area of the tapes for obtaining samples (10) in contact with the lysis buffer (20) to the buffer volume of the lysis buffer (20) contained in the chamber (210) of the biomolecule extraction device, Protein Extraction Device (PED, 1000) according to one aspect of the present invention with the ratios according to conventional devices.

In the cases of applying conventional Petri dish and Eppendorf tube, the SA:V ratios do not exceed 0.4. By comparison, in the case of applying the device of the present invention, since the cross-sectional area of the tapes (10) is 380 mm² and the amount of the lysis buffer (20) to be introduced is 200 μL when using a product such as D-Squame disk manufactured by Cuderm Corporation, the calculated SA:V ratio is 1.9, which is over 0.4, but the SA:V ratio practically exceeds 1.4 in order to secure tolerance during the manufacture of injection molding of an extractor and spare space of a mold, etc.

In theory, the SA:V ratio can be further increased by reducing a distance between the tapes for obtaining samples (10). However, considering that a target discharge amount for one time is 35~40 μl and a substantial minimum gap that can be pressed when discharging is about 100 μm, while preventing the adhesion between the two tapes (10), the SA:V ratio can be raised up to about 9.15.

As such, the present invention makes the SA:V ratio relatively high and optimal, which enables to extract proteins with a minimum amount of samples and also raise the extract concentration.

Indeed, as can be confirmed from the graph of FIG. 8, in the case of introducing the lysis buffer in the same amount (250 μl/disk) into the conventional Petri dish and Eppendorf tube, the concentration of the extracted total protein is around 40 μg/ml in both devices. However, in the case of the device according to the present invention, it can be confirmed that it scored 63.4 μg/ml, which shows noticeably higher protein extraction efficiency.

Meanwhile, the entrance of the chamber (210) may be left open or comprise a shielding film (218). In case the entrance is left open, a user introduces the lysis buffer (20) into the chamber (210) before inserting the insertion part (100); in case the entrance comprises the shielding film (218), a predetermined amount of the lysis buffer (20) may be contained inside the chamber (210) in advance.

The shielding film (218) consists of, for example, aluminum foil or vinyl film, etc., to seal the entrance of the chamber (210), and the user can insert the insertion part (100) after removing the shielding film (218), or push the insertion part (100) to penetrate the lysis buffer (218) so as to be inserted into the chamber (210). The position of the shielding film (218) is not fixed to the entrance of the chamber (21) but may be in the introduction part (230) as necessary.

An introduction part (230) may be comprised on the upper part of the chamber (210). The introduction part (230) can be configured to extend upward from the entrance of the chamber (210) by a certain height. Further, a sealing part (130) sealing the chamber (210) can be provided at one end of the insertion part (100), which is closely contacted to the inner wall of the introduction part (230) so as to correspond to the introduction part (230).

That is, the introduction part (230) is open upward, and when the tapes for obtaining samples (10) attached to the first fixing part (110) and the second fixing part (120) are inserted into the chamber (210), the sealing part (130) is fitted in the introduction part (230) to seal the chamber (210).

Further, if the introduction part (230) and the sealing part (130) are cut horizontally, the cross sections thereof may be shown in an oval shape. If the cross sections thereof are to be in a square shape, the adhesion force is not distributed evenly, and thus the sample may leak from the corners; and if the cross sections are made a circular shape, the adhesion force is distributed evenly, but they have a bulky volume. Thus, in one aspect proposes a case where the cross sections of the introduction part (230) and sealing part (30) are in an oval shape. Here, the sealing part (130) may comprise a plurality of reinforcing ribs (132) for reinforcing the strength thereof. The reinforcing ribs (132) boost the adhering force and fixing force of the sealing part (130) to the inner wall of the introduction part (230) while reinforcing the strength so that the sealing part (130) is not deformed when being joined with the body part (200).

Meanwhile, the biomolecule extraction device (1000) according to one aspect of the present invention comprises at least one discharge part (300) equipped in the insertion part (100) or body part (200). One aspect describes an example where the discharge part (300) is provided to the insertion part.

Here, the discharge part (300) comprise a discharge flow path (310) which penetrates the sealing part (310) and allows the chamber (210) to communicate with the outside and discharge the sample, and an expanded discharge port (320) which is provided at the end of the discharge flow path (310) and has an inner diameter greater than the inner diameter of the discharge flow path (310) so as to constantly discharge the sample.

The discharge flow path (310) communicates with the chamber (210) at one end and is connected to the expanded discharge port (320) at the other end, through which a sample having the protein extraction can be discharged. The discharge flow path (310) should be designed to have a minimum inner diameter before reaching the expended discharge port (320), in order to minimize the dead space and increase the total discharge amount. In one aspect, the discharge flow path (310) has a diameter of 850 μm, which is half of that of the expanded discharge port (320).

The amount of the discharged sample can be adjusted to a constant amount by adjusting the size of the inner diameter of the expanded discharge port (320). The discharge amount can be calculated according to the following equation with referring to FIG. 9. To be specific, the discharge amount can be designed by means of the equilibrium state between the gravity force based on the weight of a single droplet of the extracted sample flowing out from the expanded discharge port (320) and the surface tension thereof trying to dangle at the discharge port.

Surface tension: $F\gamma = \pi d\gamma$

Gravity force: $Fg = F\gamma \sin \alpha$ $mg = \pi d\gamma \sin \alpha$ $mg = \pi d\gamma$ $W = 2\pi r\gamma$ <Equation>

W: weight of droplet, r: radius of outlet, γ: surface tension

In one aspect, the discharge path (310) has an inner diameter of about 850 μm and the expanded discharge port (320) has an inner diameter of 1.7 mm. When the inner diameter of the expanded discharge port (320) is designed to be 1.7 mm, the unit discharge amount of the sample is theoretically about 37.7 μl.

After producing actual products, 10 biomolecule extraction devices (10) were measured and tested twice under each condition by applying deionized water and the lysis buffer (20). As a result, the actual unit discharge amount was measured as 35.5±2 μl, as shown in the following Table 1, and thus it can be confirmed that the sample is substantially constantly discharged through the biomolecule extraction devices (1000) according to the present invention.

TABLE 1

| Dev No. | D.I. water (μl) | | Lysis Buffer (μl) | |
| --- | --- | --- | --- | --- |
| | 1st droplet | 2nd droplet | 1st droplet | 2nd droplet |
| 1 | 33 | 36 | 40 | 33 |
| 2 | 33 | 36 | 35 | 35 |
| 3 | 34 | 37 | 48 | 36 |
| 4 | 33 | 33 | 35 | 36 |
| 5 | 32 | 30 | 33 | 34 |
| 6 | 35 | 35 | 35 | 36 |
| 7 | 36 | 35 | 35 | 36 |
| 8 | 37 | 38 | 37 | 35 |
| 9 | 30 | 34 | 35 | 34 |
| 10 | 30 | 34 | 35 | 37 |
| Average | 33.3 | 34.8 | 35.8 | 35.2 |
| SD | 2.3 | 2.3 | 2.0 | 1.2 |
| % CV | 6.94 | 6.47 | 5.56 | 3.49 |

As such, the biomolecule extraction devices (1000) according to one aspect of the present invention, which is a simple device without a separate metering device, is capable of precisely discharging a constant amount of sample, and thus can produce a precise experimental result in a following operation performed after the sample is discharged into a test kit after extraction.

A detachable sealing cap (140) may be additionally provided to the expanded discharge port (320), which prevents the sample from being randomly discharged and ensures the user's safety.

Meanwhile, a pressing part (212), which is formed on the outer wall of the chamber (210) such that external force can be applied when the user discharges the sample, and presses the sample, may be provided. Basically, a region corresponding to a hollow part the curved shape of the above-described first fixing part (110) forms in the outer wall of the chamber (210) forms a pressing part (212).

Specifically, the user applies pressure to the pressing part (212) to discharge the extracted sample, and when applying pressure, the inner walls of the chamber (210) are bent in a parabolic shape and thereby the extracted sample is squeezed out of the outlet.

FIG. 10 illustrates perspective views and partial cross sectional views of modifications examples of the pressing part of the biomolecule extraction device according to the aspect of the present invention, and diagrams illustrating deformation of the inner walls of the chamber when pressed.

As shown in FIG. 10, pressing parts (212a, 212b, 212c) modified in order to increase the recovery rate by applying uniform pressure are proposed.

First, in the present aspect, the pressing part (212a, 212b, 212c) may be made in an embossed form having a thickness greater than the surrounding outer wall. The pressing part (212a, 212b) may be configured to be made in a circular, embossed form as illustrated in FIGS. 10(B) and 10(C), or in a wheel shape as illustrated in FIG. 10(D). In the case of a structure having a thickness or height of 2 mm or more, a hollow is generated due to the failure to completely fill the structure of a mould with melted plastics when injection molding or the residual stress is focused when cooling after injection molding, which causes the structure's deformation or the ease generation of cracks. In the case of the pressing part in a wheel shape, the problem occurred in the injection molding can be minimized. By means of the thus-configured pressing part (212a, 212b, 212c), the sample can be discharged by applying pressure uniformly.

Further, the biomolecule extraction devices according to the aspects of the present invention may be configured to further comprise an engraved part (214) which is provided around the pressing part (212b, 212c) and has a thickness smaller than the surrounding outer wall. The engraved part (214) reduces the thickness around the pressing part (212), which enables the pressing part (212) to be easily bent.

According to the above-explained modifications, the inner wall of the chamber (210) to be pressurized is uniformly pressed from a parabolic shape in a linear manner, which can apply pressure uniformly, regardless of the shape of user's finger or the size of force to be applied, and thereby to increase the recovery rate of the sample.

FIG. 11 is a process diagram illustrating the process of extracting biomolecule (proteins) using the biomolecule extraction device according to an aspect of the present invention.

Hereinafter, we will explain a method for extracting biomolecule (proteins) by means of the biomolecule extraction device (1000) according to one aspect of the present invention, with reference to FIGS. 1 to 11.

First, two tapes for obtaining samples (10) are attached to and then detached from the subject's skin to take the skin tissue. Then, the two tapes are adhered such that they are faced each other with the first fixing part (110) and the second fixing part (120) interposed.

Then, the lysis buffer (20) is introduced into the chamber (210) of the body part (200) and the insertion part (100) is inserted into the body part (200). Here, the lysis buffer (20) is contained in the chamber (210) in advance and may be provided in a sealed state by the shielding film (218).

Thereafter, the biomolecule extraction device (1000) is shaken once or twice with the tapes for obtaining samples (10) positioned inside the chamber (210) and is left to stand for 1 minute or several minutes as necessary. In this process, the cells are dissolved in the lysis buffer (20) and the proteins are extracted.

Then, after removing the sealing cap (140), the pressing part is pressed to discharge the sample having the extracted proteins into the inlet, and the test through antibody response proceeds.

FIG. 12 is a perspective view of the biomolecule extraction device according to another aspect of the present invention. FIG. 13 is a cross sectional view of the biomolecule extraction device according to another aspect of the present invention. FIG. 14 is a plan view of the biomolecule extraction device according to another aspect of the present invention.

With reference to FIGS. 12 to 14, the biomolecule extraction device (2000) according to another aspect of the present invention may also be made by comprising an insertion part (400), a body part (500) and a discharge part (600), briefly.

Here, the discharge part (600) may be equipped in the body part (500), not in the insertion part (400), unlike the previous aspect. The insertion part (400) comprises a fixing part (410), and the tapes for obtaining samples (10) may be physically joined with the fixing part (410) by means of insertion or be adhered and fixed thereto by applying an adhesive.

One aspect suggests a case where two tapes for obtaining samples (10) are fixed to the fixing part (410), but it is also possible to fix and use a single or three or more tapes for obtaining samples (10), as necessary.

The insertion part (400) and the body part (500) may be connected to each other by a connection part (550). The body part (500) comprises an introduction part (530), and the insert part (400) may comprise a sealing part (430) to correspond to the introduction part.

Meanwhile, the body part (500) may comprise a chamber (510) which contains the lysis buffer, and the tapes for obtaining samples (10) which are fixed to the fixing part (410) can be inserted into the chamber (510) and the biomolecule can be extracted by the lysis buffer contained in the chamber (510) as the insertion part (400) is inserted into the body part (500).

Once the biomolecule extraction is completed, the user presses a pressing part (512) formed on the outer wall of the chamber (510) to discharge the extracted sample discharge through a discharge part (600). Here, various modifications explained in the previous aspect can be equally applied to the pressing part (512).

The biomolecule extraction device according to the aspects of the present invention explained so far has the following effects.

First, the biomolecule extraction device according to the present invention can perform the whole process of fixing a sample and injecting a buffer, assembling the insertion part and mixing, letting stand still and extraction, etc., within 5 minutes, which results in innovatively reducing the time to be taken, whereas most of the conventional protein or nucleic acid extraction methods required at least 20 to 30 minutes in total for mechanical or physical impact application, repetitive centrifugation, filtering and other process, etc., in order to break intercellular bonding or cell membrane.

Second, the biomolecule extraction device according to the present invention is performed in a non-impact and non-power manner, which needs neither broad experimental space nor a complicated system, ensures the user's safety, and is able to avoid harmful effect due to wastes because an extremely small amount of buffer is applied for a single use.

Third, the biomolecule extraction device according to the present invention can minimize the dead space, greatly increase the surface area:volume, which allows the protein extraction without external force in a high concentration, and constantly discharge after extraction. Thus, a precise test with a test kit is possible.

Fourth, the biomolecule extraction device according to the present invention simplifies the protein extraction process in cells and can be independently used as one device without the need of additional devices, such as a centrifuge, a pipet, etc., and can be used without the user's skill. Thus, the user's convenience can be enhanced.

In the above, the present invention was explained by referring to one example of the present invention (the example applied to the skin tissues), but a person skilled in the art can variously modify and change the present invention without deviating from the idea and scope of the present invention recited in the claims described below. The extraction device proposed in the present invention can be used for extracting from diverse biomass various biomolecules available for various analysis and diagnosis. The application scope includes biotechnology, molecular biology, medical science, pharmaceuticals, cosmetics, genetic engineering, diagnosis, health care, etc., but is not limited thereto. Thus, if the modifications basically comprise the features of the claims of the present application, they all should be deemed to belong to the technical scope of the present invention.

The invention claimed is:

1. A biomolecule extraction device comprising:
at least one tape configured to obtain a sample comprising collected biomass, the tape having an adhesive surface;
an insertion part comprising a top discharge port with a removable cap and at least one bottom fixing part to which the tape is fixed;
a body part configured to receive a lysis buffer and into which the insertion part is configured to be inserted with the top discharge port directed away from the lysis buffer and with the at least one bottom fixing part in contact with the lysis buffer to extract biomolecules from the collected biomass; and
at least one discharge part disposed in the insertion part, the discharge part comprising a discharge flow path in fluid communication on one end with the lysis buffer when the insertion part is inserted into the body part and while the biomolecule extraction device is inverted, the discharge flow path having a smaller diameter than the top discharge port and being in fluid communication on the other end with the top discharge port and being operative to discharge the lysis buffer and extracted biomolecules to the discharge port for discharge from the biomolecule extraction device; wherein
the fixing part is configured to fix the tape by adhesive bonding or physical bonding, the adhesive bonding of the fixing part being performed using the adhesiveness left on the tape after the sample is obtained, or by applying an adhesive substance to the fixing part, wherein the physical bonding of the fixing part fixes the tape by insertion of the tape into the body part.

2. The biomolecule extraction device according to claim 1,
wherein at least a portion of the fixing part has a bent or curved shape.

3. The biomolecule extraction device according to claim 1,
wherein the body part comprises a chamber having a predetermined internal space configured to receive the lysis buffer and into which the insertion part is insertable and the lysis buffer is immersed.

4. The biomolecule extraction device according to claim 3,
further comprising a shielding film configured to seal the chamber, such that the lysis buffer is retained in the chamber when the chamber is sealed.

5. The biomolecule extraction device according to claim 3,
wherein the body part further comprises an introduction part configured to guide the insertion part to the chamber.

6. The biomolecule extraction device according to claim 3,
wherein the body part further comprises an introduction part configured to guide the insertion part to the chamber and wherein the insertion part comprises a sealing part having a shape corresponding to the shape of the introduction part and configured to form a seal with an inner wall of the introduction part when the insertion part is inserted into the chamber.

7. The biomolecule extraction device according to claim 6,
wherein the sealing part comprises a reinforcing rib configured to reinforce strength thereof.

8. The biomolecule extraction device according to claim 1,
wherein the discharge flow path has an inner diameter smaller than the discharge port, such that dead space is minimized.

9. The biomolecule extraction device according to claim 1,
further comprising the removable cap is configured to detachably seal the discharge part by blocking the discharge flow path.

10. The biomolecule extraction device according to claim 3,
wherein the chamber has an outer wall, and the device further comprises a pressing part formed in the outer wall of the chamber and configured to bend when pressure is applied to the pressing part, causing a constant discharge of the sample.

11. The biomolecule extraction device according to claim 10,
wherein the pressing part is an embossed form having a thickness greater than that of the outer wall, and the biomolecule extraction device further comprises an engraved part being formed around the pressing part and having a thickness smaller than the surrounding outer wall.

12. The biomolecule extraction device according to claim 6,
wherein the cross sections of the introduction part and the sealing part have an oval or circular shape.

13. The biomolecule extraction device according to claim 1,
wherein a ratio between the surface area of the tape in contact with the lysis buffer and the volume of the lysis buffer is from 0.4 to 9.15 $mm^2/\mu L$.

14. A method for extracting biomolecules, comprising:
collecting at least one sample comprising collected biomass, with at least one tape having an adhesive surface configured for obtaining the sample;
fixing the tape to an insertion part comprising a top discharge port with a removable cap and at least one bottom fixing part to which the tape is fixed;
inserting the insertion part into a body part containing a lysis buffer with the top discharge port directed away from the lysis buffer; and
contacting the tape with the lysis buffer, resulting in the extraction of one or biomolecules from the collected biomass;
discharging the one or more biomolecules extracted from the collected biomass through a discharge part disposed in any one of the insertion part, the discharge part comprising a discharge flow path in fluid communication on one end with the lysis buffer when the insertion part is inserted into the body part and while the biomolecule extraction device is inverted, the discharge flow path having a smaller diameter than the top discharge port and being in fluid communication on the other end with the top discharge port and being operative to discharge the lysis buffer and extracted biomolecules to the discharge port for discharge from the biomolecule extraction device,
wherein the tape is fixed to the insertion part by adhesive bonding or physical bonding, wherein the adhesive bonding is performed by using the adhesiveness left on the tape after collecting the sample, or by applying an adhesive substance to ft the fixing part to which the tape is fixed, and wherein the physical bonding is performed by insertion of the tape into the body part, and
wherein the sample has a ratio between the surface area of the tape in contact with the lysis buffer and the volume of the lysis buffer that is from 0.4 to 9.15 $mm^2/\mu L$.

* * * * *